US012691073B2

(12) United States Patent
Okuda et al.

(10) Patent No.: US 12,691,073 B2
(45) Date of Patent: Jul. 28, 2026

(54) COATED SOLID PREPARATION

(71) Applicant: Towa Pharmaceutical Co., Ltd., Osaka (JP)

(72) Inventors: Yutaka Okuda, Kadoma (JP); Isamu Saeki, Kadoma (JP); Tatsuya Honjo, Kadoma (JP); Kayo Yuminoki, Kadoma (JP)

(73) Assignee: TOWA PHARMACEUTICAL CO., LTD., Osaka (JP)

( * ) Notice: Subject to any disclaimer, the term of this patent is extended or adjusted under 35 U.S.C. 154(b) by 642 days.

(21) Appl. No.: 17/277,312

(22) PCT Filed: Oct. 16, 2019

(86) PCT No.: PCT/JP2019/040556
§ 371 (c)(1),
(2) Date: Mar. 18, 2021

(87) PCT Pub. No.: WO2020/080380
PCT Pub. Date: Apr. 23, 2020

(65) Prior Publication Data

US 2021/0346301 A1 Nov. 11, 2021

(30) Foreign Application Priority Data

Oct. 19, 2018 (JP) ................................ 2018-197154

(51) Int. Cl.
*A61K 9/28* (2006.01)
*A61K 45/06* (2006.01)

(52) U.S. Cl.
CPC .......... *A61K 9/2813* (2013.01); *A61K 9/2893* (2013.01); *A61K 45/06* (2013.01)

(58) Field of Classification Search
CPC ..... A61K 9/2813; A61K 9/2893; A61K 45/06
See application file for complete search history.

(56) References Cited

U.S. PATENT DOCUMENTS

2011/0305758 A1* 12/2011 Matono ................ A61K 9/2813 424/475
2013/0337056 A1* 12/2013 Lehtonen ............. A61K 9/2893 424/490

FOREIGN PATENT DOCUMENTS

JP 2004043316 A * 2/2004
JP 2010006780 A * 1/2010
JP 2014-510066 A 4/2014
WO 2012/116814 A1 9/2012
WO 2014/044907 A1 3/2014
WO WO-2015152195 A1 * 10/2015 ........... A61K 9/0056

OTHER PUBLICATIONS

Translated JP 2010006780 A (Year: 2010).*
Translated WO 2015152195 A1 (Year: 2015).*
https://korvustech.com/evaporation-vs-sputtering/ (Year: 2023).*
Sah et al. (Tablet Coating Technology: An Overview, Asian Journal of Pharmacy and Technology, 2014). (Year: 2014).*
https://spflist.com/mineral-sunscreens/iron-oxide#:~:text=Research%20demonstrates%20that%20formulations%20with,combined%20with%20mineral%20UV%20filters. (Year: 2025).*
https://www.pharmaexcipients.com/wp-content/uploads/attachments/Colours-in-Pharmaceutical-products-printout-MC.pdf?t=1463001681 (Year: 2013).*
International Search Report issued in corresponding International Patent Application No. PCT/JP2019/040556 dated Dec. 10, 2019.

* cited by examiner

*Primary Examiner* — Andrew S Rosenthal
*Assistant Examiner* — Danielle Kim
(74) *Attorney, Agent, or Firm* — Morgan, Lewis & Bockius LLP

(57) ABSTRACT

The present disclosure provides a pharmaceutical solid preparation containing at least one pharmaceutically active ingredient, wherein the surface of the solid preparation is coated with a light shielding agent or a metal oxide, and a process for producing a solid preparation containing at least one pharmaceutically active ingredient, comprising a step of coating a light shielding agent or a metal oxide.

20 Claims, 1 Drawing Sheet

[Figure 1]
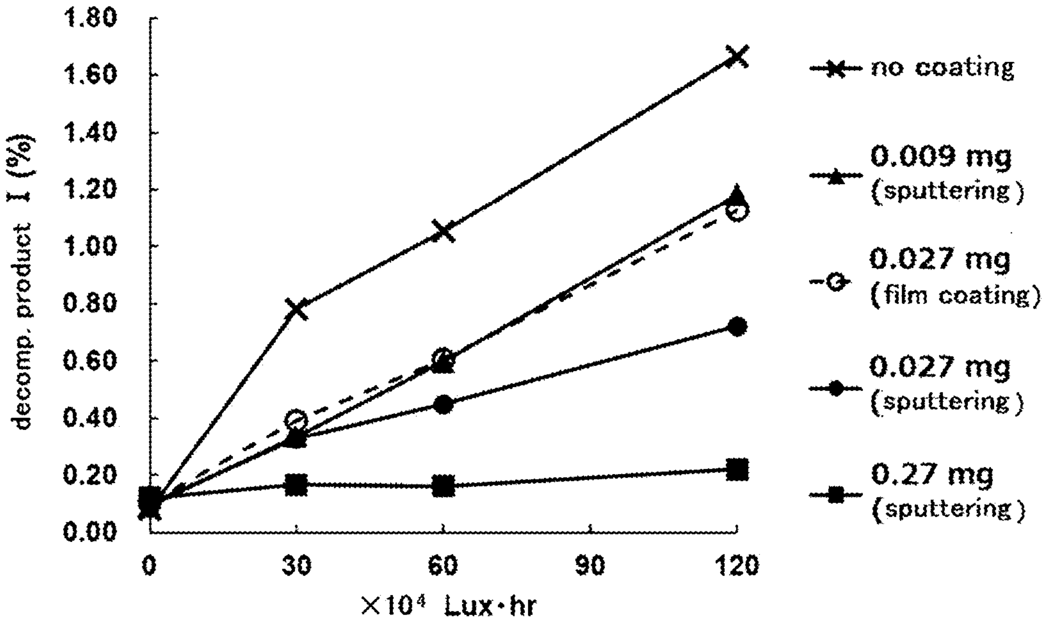
[Figure 2]
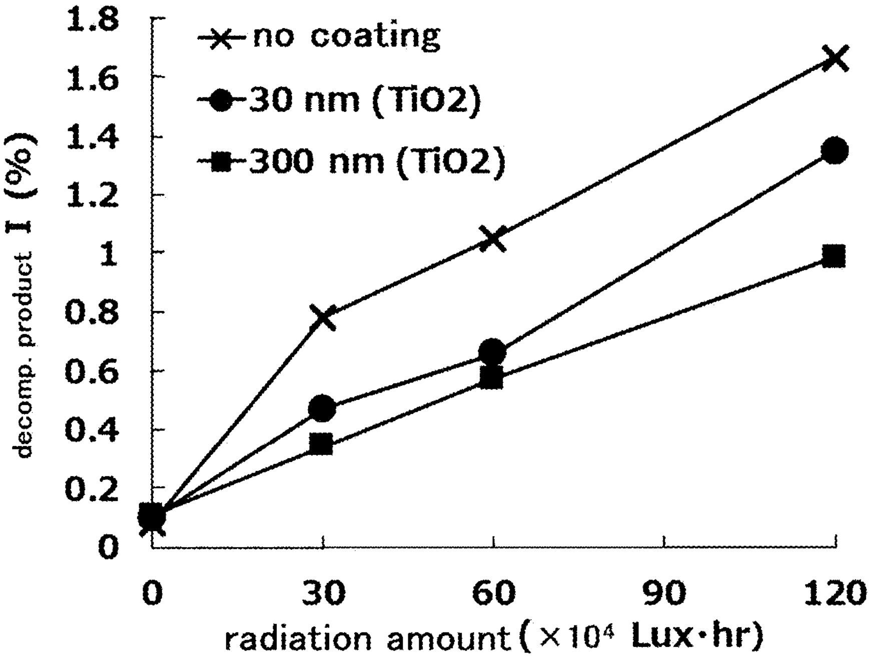

COATED SOLID PREPARATION

CROSS-REFERENCE TO RELATED APPLICATIONS

This application claims the benefit of Japanese Patent Application No. 2018-197154, filed Oct. 19, 2018 with Japan Patent Office. The Japanese application is hereby incorporated by reference for all purposes as if the entire application documents (specification, claims, drawings, and abstract) were expressly set forth herein.

TECHNICAL FIELD

The present invention belongs to the technical field of pharmaceutical preparations containing a pharmaceutical active ingredient. The present invention relates to, for example, a coated solid preparation containing at least one pharmaceutically active ingredient, which is excellent in disintegration properties while ensuring photostability of the medicine.

BACKGROUND OF THE INVENTION

Pharmaceutical solid preparations are coated, for example, to protect a drug from moisture, oxygen, carbon dioxide, light, etc. in the atmosphere, to control the release or modulate the onset of action of a drug, to mask taste or smell of a drug and make it easier to take a drug, to increase commercial value of a drug, or to increase distinctiveness of a drug. In pharmaceuticals, the above coating has been conventionally performed mainly by film coating or sugar coating. A film coating is one in which an aqueous solution or an organic solvent solution containing a polymer (coating agent) of a coating base is sprayed continuously or discontinuously on the surface of a solid preparation, and a moisture or an organic solvent of a droplet adhering to and spreading on the surface of the solid preparation is evaporated, whereby the coating agent particles aggregate and form a film.

In particular, in the case of a film coating, since the layer is applied to the periphery of a solid preparation at a micro-order thickness, the disintegration time tends to be longer than that of an uncoated plain tablet or the like. Thus, the elution of the drug from the solid preparation may be delayed. Also, for example, when a light shielding agent is coated to protect a drug from light, the film coating must be executed with a polymer compound such as hypromellose or hydroxypropyl cellulose.

As a technique for coating a pharmaceutical solid preparation, in addition to the above, a method called an atomic layer deposition method (ALD) is known (Patent Document 1). Such an atomic layer deposition method is a method in which a functional group present on the surface of a pharmaceutical preparation reacts with a coating material, and a film of a monomolecular layer is laminated by vapor deposition. In Patent Document 1, using such an atomic layer deposition method, a metal oxide layer is formed on a pharmaceutical solid preparation containing an active ingredient with a nano-order thickness of about 0.1 nm to about 100 nm to coat the pharmaceutical solid preparation.

On the other hand, sputtering is one of the metal film-forming techniques also called dry plating or vacuum plating. This is a technology to form a thin film, in which an inert gas (e.g., argon) is introduced in a vacuum, a negative voltage is applied to the target (plate-shaped film forming material) to generate a glow discharge, the inert gas atom is ionized, the gas ions are made to collide with the surface of the target at a high speed and hit it violently, and the particles (atoms and molecules) of the film-forming material constituting the target are vigorously ejected and vigorously adhered and deposited on the surface of the base material/substrate. It is applied to antireflection and surface protection of displays such as televisions and smartphones, transparent electrodes of solar cells and liquid crystal devices, conferring of abrasion resistance, and suppression of permeation of water vapor and oxygen.

As compared with the atomic layer deposition method (ALD), sputtering is characterized in that the adhesion force of the film is strong and the film stress is large. In addition, the sputtering technique has an advantage that the film forming material is hardly changed in quality and heat is hardly applied to the object.

Sputtering techniques have also been applied in the field of pharmaceuticals or foods. For example, Patent Document 2 discloses that a metal film made of an edible metal such as gold, silver, or platinum is formed on the surface of a granular shape, a tablet shape or the like, and a medicine or the like having excellent decorativeness is provided. However, the invention of Patent Document 2 is not carried out from the viewpoint of shielding a pharmaceutical solid preparation from light and imparting functionality.

PRIOR ART

Patent Document

Patent Document 1: JP, 2014-510066, A
Patent Document 2: JP, 2004-43316, A

SUMMARY OF THE INVENTION

Problems to be Solved by the Invention

The present invention is, for example, primarily directed to providing a novel solid preparation containing a pharmaceutically active ingredient, wherein the solid preparation is coated with a light shielding agent or a metal oxide in a nano-order thickness.

Means for Solving the Problems

As a result of intensive studies, the present inventors have found that the above problem can be solved by using a sputtering technique for coating a pharmaceutical solid preparation, and the present invention was completed.

The present invention can include, for example, the following.

[1] A pharmaceutical solid preparation containing at least one pharmaceutically active ingredient, wherein the surface of the solid preparation is coated with a light shielding agent or a metal oxide to a thickness in a range of 1 nm to 500 nm to form a coating layer.

[2] A pharmaceutical solid preparation containing at least one pharmaceutically active ingredient, wherein the surface of the solid preparation is coated with a light shielding agent or a metal oxide which is present in a range of $5\times10^{-6}$ mg/mm$^2$ to $3\times10^{-3}$ mg/mm$^2$ to form a coating layer.

[3] The pharmaceutical solid preparation according to [1] or [2] above, wherein the coating layer comprises no polymer compound.

[4] The pharmaceutical solid preparation according to any one of [1] to [3] above, wherein the coating is performed by sputtering.

[5] The pharmaceutical solid preparation according to any one of [1] to [4] above, wherein the metal oxide is iron oxide or titanium oxide.

[6] The pharmaceutical solid preparation according to any one of [1] to [5] above, wherein the solid preparation is a tablet.

[7] The pharmaceutical solid preparation according to [6] above, of which the disintegration time is substantially the same as that of the tablet before the coating.

[8] A process for producing a solid preparation containing at least one pharmaceutically active ingredient, comprising a step of coating a light shielding agent or a metal oxide by sputtering on the surface of the solid preparation to a thickness in a range of 1 nm to 500 nm.

[9] A process for producing a solid preparation containing at least one pharmaceutically active ingredient, comprising a step of coating a light shielding agent or a metal oxide by sputtering on the surface of the solid preparation so as to be present in a range of $5\times10^{-6}$ mg/mm$^2$ to $3\times10^{-3}$ mg/mm$^2$.

[10] The process for producing a pharmaceutical solid preparation according to [8] or [9] above, wherein the metal oxide is iron oxide or titanium oxide.

[11] The process for producing a pharmaceutical solid preparation according to any one of [8] to [10] above, wherein the solid preparation is a tablet.

[12] The process for producing a pharmaceutical solid preparation according to [11] above, of which the disintegration time is substantially the same as that of the tablet before the coating.

[13] A method for photostabilizing a pharmaceutical solid preparation containing at least one pharmaceutically active ingredient, comprising a step of coating a light shielding agent or a metal oxide by sputtering on the surface of the solid preparation to a thickness in a range of 1 nm to 500 nm.

[14] A method for photostabilizing a pharmaceutical solid preparation containing at least one pharmaceutically active ingredient, comprising a step of coating a light shielding agent or a metal oxide by sputtering on the surface of the solid preparation so as to be present in a range of $5\times10^{-6}$ mg/mm$^2$ to $3\times10^{-3}$ mg/mm$^2$.

[15] The method for photostabilizing a pharmaceutical solid preparation according to [13] or [14] above, wherein the metal oxide is iron oxide or titanium oxide.

[16] The method for photostabilizing a pharmaceutical solid preparation according to any one of [13] to [15] above, wherein the solid preparation is a tablet.

Effect of the Invention

According to the present invention, for example, it is possible to provide pharmaceutical solid preparations excellent in disintegration properties while ensuring photostability of medicines.

BRIEF DESCRIPTION OF THE DRAWINGS

FIG. 1 represents the results of photostability. The vertical axis indicates the amount generated (%) of the decomposition product I (described later), and the horizontal axis indicates the light irradiation amount (×10,000 Lux·hr), respectively. Black triangles indicate the result of Example 1, black circles indicate the result of Example 2, black squares indicate the result of Example 3, cross marks indicate the result of Comparative Example 1 (uncoated plain tablets), and white circles indicate the result of Comparative Example 2 (film-coated tablets), respectively.

FIG. 2 represents the results of photostability. The vertical axis indicates the amount of decomposition product I generated (%) and the horizontal axis indicates the light irradiation amount (×10,000 Lux·hr). Black squares indicate the result of Example 4, black circles indicate the result of Example 5, and cross marks indicate the result of Comparative Example 1 (uncoated plain tablets), respectively.

EMBODIMENT FOR CARRYING OUT THE PRESENT INVENTION

1 Pharmaceutical Solid Preparations According to the Present Invention

A pharmaceutical solid preparation according to the present invention (hereinafter, referred to as the "present invention preparation") is a solid preparation containing at least one pharmaceutically active ingredient, wherein the surface of the solid preparation is coated with a light shielding agent or a metal oxide to a thickness in a range of 1 nm to 500 nm to form a coating layer. The present invention preparation is also a solid preparation containing at least one pharmaceutically active ingredient, wherein the surface of the solid preparation is coated with a light shielding agent or a metal oxide which is present in a range of $5\times10^{-6}$ mg/mm$^2$ to $3\times10^{-3}$ mg/mm$^2$ to form a coating layer.

In the present invention preparation, the pharmaceutically active ingredient is not particularly limited, as long as it is a medicine having pharmacological activity, but photolabile pharmaceutically active ingredients are preferred. Such active ingredients may include, for example, calcium antagonists such as Nifedipine, Amlodipine, Nicardipine, and Azelnidipine, and HMG-CoA reductase inhibitors such as vitamins, Atorvastatin, Pitavastatin, and Rosuvastatin.

In the present invention preparation, the light shielding agent or the metal oxide is not particularly limited, as long as it is pharmaceutically acceptable and can be sputtered, but metal oxides are suitable. The light shielding agent or the metal oxide used in the present invention can include iron oxides such as red ferric oxide, yellow ferric oxide, yellow iron oxide, and black iron oxide; silicon dioxide; and titanium oxide. Among them, yellow ferric oxide, red ferric oxide, and titanium oxide are preferred.

In the present invention, the light shielding agent or the metal oxide is coated (nanocoated) on the surface of the solid preparation with a thickness in a range of 1 nm to 500 nm to form a coating layer, and the thickness is preferably in a range of 5 nm to 400 nm, and more preferably in a range of 10 nm to 300 nm. If it is thinner than 1 nm, a sufficient light shielding effect may not be obtained, and if it is thicker than 500 nm, the manufacturing time may extend for a long time. Alternatively, in the present invention, the light shielding agent or the metal oxide is coated (nanocoated) on the surface of the solid preparation so as to be present in a range of $5\times10^{-6}$ mg/mm$^2$ to $3\times10^{-3}$ mg/mm$^2$ to form a coating layer, and the amount is preferably in a range of $2\times10^{-5}$ mg/mm$^2$ to $2\times10^{-3}$ mg/mm$^2$, and more preferably in a range of $5\times10^{-5}$ mg/mm$^2$ to $1.5\times10^{-3}$ mg/mm$^2$. If it is less than $5\times10^{-6}$ mg/mm$^2$, a sufficient light-shielding effect may not be obtained, and if it is more than $3\times10^{-3}$ mg/mm$^2$, the manufacturing time may extend for a long time.

As described above, since the light shielding agent or the metal oxide is coated on the nano-order in the present invention, for example, the disintegration time of the tablet before the coating (uncoated plain tablets, film-coated tablets, or the like) and the nanocoated tablet after the coating can be substantially the same. The term "substantially the same" as to the disintegration time herein means that the disintegration time of the nanocoated tablet after the coating is in a range of 0.5 to 1.5 times that of the tablet before the coating. It is preferably in a range of 0.8 to 1.2 times. The disintegration time can be measured according to the test method described in the Japanese Pharmacopoeia.

The dosage form of the present invention preparation is not particularly limited, as long as it is a pharmaceutical solid preparation, and examples thereof can include tablets, granules, powders, pellets, capsules, chewable tablets, troches, and film preparations. Among them, tablets are preferred. Tablets may be not only conventional tablets, but also multilayer tablets such as bilayer tablets and trilayer tablets, enteric coated tablets, sustained release tablets, so-called OD tablets such as orally disintegrating tablets, and OD films.

The nanocoating of the light shielding agent or the metal oxide is usually performed by sputtering. Sputtering itself is a known method, and the sputtering can be performed by the known method in the present invention, too. For example, a strong magnetic field is applied in a vacuum having a light shielding agent, argon is introduced into the vacuum, and ionized (Ar+) by the magnetic field, and atoms and molecules on the surface of the light shielding agent are ejected by causing the ionized argon to collide with the light shielding agent, and thereby the atoms and molecules reach the surface of the pharmaceutical solid preparation to be coated and are formed into a film. Apparatus for performing the sputtering is commercially available, and it is possible to perform the sputtering using them.

2 Process for Producing Pharmaceutical Solid Preparations According to the Present Invention The process for producing a solid pharmaceutical preparation according to the present invention (hereinafter referred to as the "present invention process") is a process for producing a pharmaceutical solid preparation containing at least one pharmaceutically active ingredient, characterized by comprising a step of coating a light shielding agent or a metal oxide by sputtering on the surface of the solid preparation to a thickness in a range of 1 nm to 500 nm. The present invention process is also characterized by comprising a step of coating a light shielding agent or a metal oxide by sputtering on the surface of the solid preparation so as to be present in a range of $5\times10^{-6}$ mg/mm$^2$ to $3\times10^{-3}$ mg/mm$^2$.

In the present invention process, first, a pharmaceutical solid preparation before the coating (uncoated plain tablets, film-coated tablets, or the like) is produced. Specifically, for example, a pharmaceutical solid preparation before the coating (e.g., uncoated plain tablets and film-coated tablets) is produced through steps of mixing at least one kind of pharmaceutically active ingredient with additives such as an excipient, a binder, a disintegrant, a stabilizer, and a colorant depending on the dosage form and the like, granulating, drying, sizing, adding a lubricant and the like, and tableting them, and if necessary, a step of film coating them with a coating agent containing a polymer, and other steps. Thereafter, the present invention process can be carried out by coating a light shielding agent or a metal oxide by sputtering on the surface of the pharmaceutical solid preparation before the coating (uncoated plain tablets, film-coated tablets, etc.) to a thickness in a range of 1 nm to 500 nm (preferably 5 nm to 400 nm, and more preferably 10 nm to 300 nm), or so as to be present in a range of $5\times10^{-6}$ mg/mm$^2$ to $3\times10^{-3}$ mg/mm$^2$ (preferably $2\times10^{-5}$ mg/mm$^2$ to $2\times10^{-3}$ mg/mm$^2$, and more preferably $5\times10^{-5}$ mg/mm$^2$ to $1.5\times10^{-3}$ mg/mm$^2$).

The meanings of the pharmaceutically active ingredient, the solid preparation, the sputtering, the light shielding agent, the metal oxide, and the like in the present invention process are the same as described above.

Excipients used in the present invention can include lactose, starch (e.g., corn starch, potato starch, rice starch, and wheat starch), crystalline cellulose, D-mannitol, dextrin, sorbitol, calcium phosphate anhydride, white sugar, talc (natural hydrous magnesium silicate), kaolin, precipitated calcium carbonate, sodium chloride, titanium oxide, and light anhydrous silicic acid, for example.

Binding agents used in the present invention can include hydroxypropyl cellulose, hypromellose (hydroxypropyl methylcellulose, HPMC), microcrystalline cellulose, dextrin, tragacanth, gelatin, alphaized starch, gum arabic, acacia, alginic acid, carboxymethyl cellulose, ethyl cellulose, methylcellulose, hydroxyethyl cellulose, ethyl hydroxyethyl cellulose, polyvinylpyrrolidone, polyvinyl alcohol, polyacrylate, carboxymethyl cellulose calcium, and sodium carboxymethyl cellulose, for example.

Stabilizing agents used in the present invention can include butylhydroxytoluene (BHT), propyl gallate, butylhydroxyanisole (BHA), lecithin, α-tocopherol, hydroquinone, octyl gallate, dodecyl gallate, isoamyl gallate, nordihydroguaiaretic acid, guaiac fat, α-naphthylamine, ascorbate palmitate, cysteine hydrochloride, sodium stearate ascorbate, thioglycerol, and thiosorbitol, for example.

Disintegrants used in the present invention can include croscarmellose sodium, crospovidone, alginic acid, carboxymethyl cellulose calcium, sodium carboxymethyl cellulose, microcrystalline cellulose, hydroxypropyl cellulose, low substituted hydroxypropyl cellulose, crosslinked polyvinylpyrrolidone, sodium alginate, sodium starch glycolate, partially hydrolyzed starch, and an agar powder, for example.

Lubricants used in the present invention can include magnesium stearate, calcium stearate, talc, mineral oil, stearic acid, fumaric acid, polyethylene glycol, calcium, boric acid, paraffin, and cocoa butter, for example.

Pigments used in the present invention can include tar dye, red ferric oxide, red iron oxide, yellow iron oxide, titanium dioxide, inorganic dye, red No. 3, red No. 20, yellow No. 6, blue No. 2, green No. 5, orange No. 5, red No. 8, and caramel which can be used in pharmaceuticals and the like, as stipulated by the Ministry of Health, Labor and Welfare ordinance, for example.

Each of the above additives may be used either alone or in combination of one or any two or more kinds thereof. Further, each of them can be used in an appropriate amount as needed.

According to the present invention process, since the light shielding agent or the metal oxide is coated in the nano-order on the tablet before the coating (uncoated plain tablets, film-coated tablets, or the like), it is possible to produce the tablet having substantially the same disintegration time as that of the tablet before the coating.

3 Photostablizing Methods for Pharmaceutical Solid Formulations

The method for photostabilizing a pharmaceutical solid preparation according to the present invention (hereinafter referred to as the "photostabilization method of the present invention") is a method for photostabilizing a solid preparation containing at least one pharmaceutically active ingredient, characterized by comprising a step of coating a light shielding agent or a metal oxide by sputtering on the surface of the solid preparation to a thickness in a range of 1 nm to 500 nm. The photostabilization method of the present invention is also characterized by comprising a step of coating a light shielding agent or a metal oxide by sputtering on the surface of the solid preparation so as to be present in a range of $5\times10^{-6}$ mg/mm$^2$ to $3\times10^{-3}$ mg/mm$^2$.

The photostabilization method of the present invention can be carried out at least by coating a light shielding agent or a metal oxide by sputtering on the surface of the pharmaceutical solid preparation such as tablets to a thickness in a range of 1 nm to 500 nm (preferably 5 nm to 400 nm, and more preferably 10 nm to 300 nm), or so as to be present in a range of $5\times10^{-6}$ mg/mm$^2$ to $3\times10^{-3}$ mg/mm$^2$ (preferably $2\times10^{-5}$ mg/mm$^2$ to $2\times10^{-3}$ mg/mm$^2$, and more preferably $5\times10^{-5}$ mg/mm$^2$ to $1.5\times10^{-3}$ mg/mm$^2$).

The meanings of the pharmaceutically active ingredient, the solid preparation, the sputtering, the light shielding agent, the metal oxide, and the like in the photostabilization method of the present invention are the same as described above.

EXAMPLE

Hereinafter, the present invention will be described with reference to Examples, Comparative Examples, Test Examples, and the like, but the present invention is not limited by these Examples and the like in any way.

[Comparative Example 1, Examples 1 to 3] Preparations of Uncoated Plain Tablets and Nanocoated Tablets with Red Ferric Oxide In accordance with the formulations in Tables 1 and 2 below, the uncoated plain tablet of Comparative Example 1 and the tablets of Examples 1 to 3, the present invention preparations, were prepared by being nanocoated with red ferric oxide to a thickness of about 10 nm to 300 nm or so that the red ferric oxide is present in $5.23\times10^{-5}$ mg/mm$^2$ to $1.57\times10^{-3}$ mg/mm$^2$.

TABLE 1

| Composition | Ingredient | Blending amount (mg) Comp. Example 1, Examples 1 to 3 |
|---|---|---|
| (A) active granules | Amlodipine besilate | 6.93 |
| | excipient | 52.87 |
| | pigment | 0.2 |
| (A) active granules total | | 60 |
| (B) fast disintegrating granules | excipient | 130.8 |
| | disintegrant | 3.6 |
| | pigment | 0.2 |
| (B) fast disintegrating granules total | | 134.6 |
| (C) flavoring granules | excipient | 1.7 |
| | taste modifier | 0.5 |
| (C) flavoring granules total | | 2.2 |

TABLE 2

| Composition | Ingredient | Blending amount (mg) Comp. Example 1 | Examples 1 to 3 |
|---|---|---|---|
| Tablet | (A) active granules | 60 | 60 |
| | (B) fast disintegrating granules | 134.6 | 134.6 |
| | (C) flavoring granules | 2.2 | 2.2 |
| | lubricant | 1.9 | 1.9 |
| | sweeting agent | 5.3 | 5.3 |
| | perfume | 1 | 1 |
| Tablet total | | 205 | 205 |
| Coating | red ferric oxide | — | trace (*) |
| Total | | 205 | 205 |

(*) Example 1 (10 nm in film thickness): 0.009 mg/tablet, $5.23\times10^{-5}$ mg/mm$^2$
Example 2 (30 nm in film thickness): 0.027 mg/tablet, $1.57\times10^{-4}$ mg/mm$^2$
Example 3 (300 nm in film thickness): 0.27 mg/tablet, $1.57\times10^{-3}$ mg/mm$^2$ Specifically, the uncoated plain tablet of Comparative Example 1 and the red ferric oxide-nanocoated tablets of Examples 1 to 3 were produced as follows.

(1) Preparation of Tablets (A) Active granules, (B) fast disintegrating granules, (C) sweetening agent granulated into flavoring granules, and perfume were placed in a diffusion type mixer and mixed, and then a granulated lubricant was added and further mixed to obtain a tablet powder. The tablet of Comparative Example 1 was obtained by tableting the tablet powder so as to have a punch diameter of 8.5 mm and a tablet mass of 205 mg.

(2) Nanocoating: Preparation of Tablets of Examples 1 to 3

The tablet (uncoated plain tablet) of Comparative Example 1 was coated with a predetermined amount of red ferric oxide using a magnetron type sputtering apparatus (product number: L560, manufactured by Leybold Co.) to produce the nanocoated tablets of Examples 1 to 3 of the present invention preparation.

[Comparative Example 2] Film-Coated Tablets

A mixture of TC-5 (hypromellose, 5.7 mg/tablet) and red ferric oxide (0.027 mg/tablet) was prepared, with which the tablet of Comparative Example 1 was film-coated by a conventional method to produce the film-coated tablet of Comparative Example 2.

[Test Example 1] Physical Properties of Tablets

Physical properties of the obtained tablets of Examples 1 to 3 and Comparative Examples 1 and 2 were measured by a conventional method (n=3). The results are shown in Table 3 below.

TABLE 3

| | Example 1 | Example 2 | Example 3 | Comp. Example 1 | Comp. Example 2 |
|---|---|---|---|---|---|
| Coating method | sputtering | sputtering | sputtering | — | film coating |
| Thickness of layer | 10 nm | 30 nm | 300 nm | — | 0.12 mm |
| Coating amount of $Fe_2O_3$ (mg/tablet) | 0.009 | 0.027 | 0.27 | 0 | 0.027 |
| Hardness (N) | 59 | 63 | 63 | 73 | 131 |

TABLE 3-continued

| | Example 1 | Example 2 | Example 3 | Comp. Example 1 | Comp. Example 2 |
|---|---|---|---|---|---|
| Disintegration time (s) | 20 | 18 | 21 | 19 | 86 |

As is apparent from Table 3, all of the present invention preparations of Examples 1 to 3 had a disintegration time faster than that of a conventional film-coated tablet (Comparative Example 2) and almost equivalent to that of an uncoated plain tablet (Comparative Example 1), and had excellent disintegration properties.

[Test Example 2] Photostability Test

The tablets of Examples 1 to 3 and Comparative Examples 1 and 2 were placed in a photostability tester, and a photostability test was performed by a xenon lamp irradiation with 0.3 to 1.2 million lx·hr under a condition of 70% RH at 25° C. The results are shown in Table 5 and FIG. 1. The amount of the decomposition product I having the following structural formula was measured by high performance liquid chromatography (HPLC). The measurement conditions are as follows.

[Chemical 1]

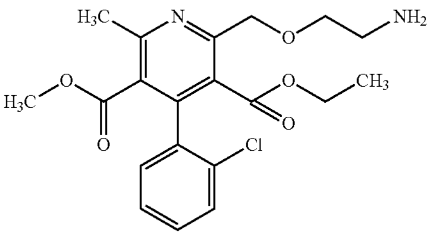

[HPLC Measurement Conditions]

Detector: Waters2487, ultraviolet absorption photometer (measured at 237 nm)

Column: Cadenza CD C18, A stainless steel column having an inner diameter of 4.6 mm and a length of 15 cm, packed with octylsilanized silica gel for liquid chromatography (3 μm in particle diameter).

Column temperature: A constant temperature around 35° C.

Sample temperature: A constant temperature around 4° C.

Mobile phase: A mixed solution of potassium dihydrogen phosphate aqueous solution and acetonitrile

TABLE 4

| Time (min) | Potassium dihydrogen phosphate aqueous solution (%) | Acetonitrile (%) |
|---|---|---|
| 0 to 15 | 80 → 50 | 20 → 50 |
| 15 to 20 | 50 → 20 | 50 → 80 |
| 20 to 25 | 20 | 80 |
| 25 to 26 | 20 → 80 | 80 → 20 |
| 26 to 30 | 80 | 20 |

Flow rate: 1.0 mL/min

Analysis time: 30 minutes

TABLE 5

| | | | Example 1 | Example 2 | Example 3 | Comp. Example 1 | Comp. Example 2 |
|---|---|---|---|---|---|---|---|
| Coating method | | | sputtering | sputtering | sputtering | — | film coating |
| Coating amount of $Fe_2O_3$ (mg/tablet) | | | 0.009 | 0.027 | 0.27 | 0 | 0.027 |
| Photostability | 0 | Decomp. | 0.09 | 0.10 | 0.12 | 0.08 | 0.10 |
| test | 30 | product I | 0.34 | 0.33 | 0.17 | 0.78 | 0.39 |
| ($\times 10^4$ lx · hr) | 60 | (%) | 0.60 | 0.45 | 0.16 | 1.05 | 0.61 |
| | 120 | | 1.18 | 0.72 | 0.22 | 1.67 | 1.13 |

As is apparent from Table 5 and FIG. 1, all of the present invention preparations of Examples 1 to 3 were excellent in photostability, which was superior to that of the uncoated plain tablet of Comparative Example 1, and equivalent to or higher than that of the conventional film-coated tablet of Comparative Example 2. With only a 30 nm coating of red ferric oxide (Example 2), the increase in the photodecomposition product was halved from that of the uncoated plain tablet of Comparative Example 1. In addition, as is apparent from the comparison of Example 2 and Comparative Example 2, in which the coating amount of red ferric oxide is the same, the present invention has a smaller amount of increase in photolysate than a conventional film coating and is excellent in photostability.

[Examples 4 and 5] Preparation of Nanocoated Tablets by Titanium Oxide

The uncoated plain tablet of Comparative Example 1, and the tablets of Examples 4 and 5, the present invention preparations, nanocoated with titanium oxide to a thickness of about 30 nm or 300 nm or so that titanium oxide is present in $1.2\times10^{-4}$ mg/mm$^2$ or $1.2\times10^{-3}$ mg/mm$^2$ were prepared according to the formulation of Table 6 below.

TABLE 6

| Composition | Ingredient | Blending amount (mg) Examples 4, 5 |
|---|---|---|
| Tablet | (A) active granules | 60 |
| | (B) fast disintegrating granules | 134.6 |
| | (C) flavoring granules | 2.2 |
| | lubricant | 1.9 |

TABLE 6-continued

| Composition | Ingredient | Blending amount (mg) Examples 4, 5 |
|---|---|---|
| | sweeting agent | 5.3 |
| | perfume | 1 |
| Tablet total | | 205 |
| Coating | titanium oxide | trace (**) |
| Total | | 205 |

(**) Example 4 (30 nm in film thickness): 0.0205 mg/tablet, $1.2 \times 10^{-4}$ mg/mm$^2$
Example 5 (300 nm in film thickness): 0.205 mg/tablet, $1.2 \times 10^{-3}$ mg/mm$^2$ Specifically, the uncoated plain tablet of Comparative Example 1 was coated with a predetermined amount of titanium oxide using a magnetron type sputtering apparatus (product number: L560, manufactured by Leybold Co.) to produce the nanocoated tablets of Examples 4 and 5 of the present invention preparation.

[Test Example 3] Physical Properties of Tablets

Physical properties of the obtained tablets of Examples 4 and 5, and Comparative Example 1 were measured by a conventional method (n=3). The results are shown in Table 7 below.

TABLE 7

| | Example 4 | Example 5 | Comp. Example 1 |
|---|---|---|---|
| Thickness of layer | 30 nm | 300 nm | — |
| Coating amount of $TiO_2$ (mg/tablet) | 0.0205 | 0.205 | 0 |
| Hardness (N) | 51 | 52 | 73 |
| Disintegration time (s) | 20 | 20 | 19 |

As is apparent from Table 7, all of the present invention preparations of Examples 4 and 5 had almost the same disintegration time as that of the uncoated plain tablet (Comparative Example 1), and were excellent in disintegration properties.

[Test Example 4] Photostability Test

The tablets of Examples 4 and 5 were placed in a photostability tester, and a photostability test was performed by a xenon lamp irradiation with 0.3 to 1.2 million lx·hr under 70% RH conditions at 25° C. The results are shown in Table 8 and FIG. 2. Under the same measurement conditions as in Test Example 2 described above, the amount of the decomposition product I was measured by high performance liquid chromatography (HPLC).

TABLE 8

| | | | Example 4 | Example 5 | Comp. Example 1 |
|---|---|---|---|---|---|
| Coating amount of $TiO_2$ (mg/tablet) | | | 0.0205 | 0.205 | 0 |
| Photostability | 0 | Decomp. | 0.10 | 0.11 | 0.08 |
| test | 30 | product I | 0.47 | 0.34 | 0.78 |
| ($\times 10^4$ lx · hr) | 60 | (%) | 0.66 | 0.58 | 1.05 |
| | 120 | | 1.35 | 0.99 | 1.67 |

As is apparent from Table 8 and FIG. 2, all of the present invention preparations of Examples 4 and 5 exhibited higher photostability than that of the uncoated plain tablet of Comparative Example 1. Even with only a 30 nm coating of titanium oxide (Example 4), the increase of the photolysate amount is greatly suppressed as compared with the uncoated plain tablet of Comparative Example 1.

INDUSTRIAL APPLICABILITY

According to the present invention, for example, it is possible to provide a pharmaceutical solid preparation having excellent disintegration properties while ensuring photostability of a medicine, and therefore the present invention is useful in a pharmaceutical solid preparation containing an active ingredient which is unstable to light, or useful in the production thereof.

The invention claimed is:

1. A pharmaceutical solid preparation containing at least one pharmaceutically active ingredient, wherein the solid preparation has a coating layer having a thickness from 1 nm to less than 500 nm, consisting of physically deposited metal oxide particles on a surface of the solid preparation, wherein a total amount of the metal oxide particles is from $5\times10^{-6}$ mg/mm$^2$ to $3\times10^{-3}$ mg/mm$^2$.

2. The pharmaceutical solid preparation according to claim 1, wherein the coating layer comprises no polymer compound.

3. The pharmaceutical solid preparation according to claim 1, wherein the metal oxide particles are physically deposited on the surface of the solid preparation by sputtering.

4. The pharmaceutical solid preparation according to claim 1, wherein the metal oxide particles comprise iron oxide particles.

5. The pharmaceutical solid preparation according to claim 1, wherein the solid preparation is a tablet.

6. The pharmaceutical solid preparation according to claim 5, of which a disintegration time is substantially the same as that of the tablet before the coating.

7. A process for producing the pharmaceutical solid preparation of claim 1, comprising sputtering the metal oxide particles on the surface of the solid preparation in an amount of $5\times10^{-6}$ mg/mm$^2$ to $3\times10^{-3}$ mg/mm$^2$ to form the coating layer.

8. The process for producing a pharmaceutical solid preparation according to claim 7, wherein the metal oxide particles comprise iron oxide particles and/or titanium oxide particles.

9. The process for producing a pharmaceutical solid preparation according to claim 7, wherein the solid preparation is a tablet.

10. The process for producing a pharmaceutical solid preparation according to claim 9, of which a disintegration time is substantially the same as that of the tablet before the coating.

11. A method for photostabilizing the pharmaceutical solid preparation of claim 1, comprising sputtering the metal oxide particles on the surface of the solid preparation in an amount of $5\times10^{-6}$ mg/mm$^2$ to $3\times10^{-3}$ mg/mm$^2$ to form the coating layer.

12. The method for photostabilizing a pharmaceutical solid preparation according to claim 11, wherein the metal oxide particles comprise iron oxide particles and/or titanium oxide particles.

13. The method for photostabilizing a pharmaceutical solid preparation according to claim 11, wherein the solid preparation is a tablet.

14. The pharmaceutical solid preparation according to claim 1, wherein the metal oxide particles comprise red ferric oxide particles.

15. The pharmaceutical solid preparation according to claim 1, wherein the metal oxide particles comprise titanium oxide particles.

16. The pharmaceutical solid preparation according to claim 1, wherein the coating layer has a thickness from 10 nm to 400 nm.

17. The pharmaceutical solid preparation according to claim 1, wherein the thickness is from 100 nm to 300 nm.

18. The pharmaceutical solid preparation according to claim 1, wherein the metal oxide particles comprise at least one metal oxide selected from the group consisting of iron oxide, titanium dioxide, and silicon dioxide.

19. The pharmaceutical solid preparation according to claim 1, wherein the at least one pharmaceutically active ingredient comprises a photolabile pharmaceutically active ingredient.

20. The pharmaceutical solid preparation according to claim 1, wherein the metal oxide particles are physically deposited on the surface of the solid preparation by sputtering; wherein the metal oxide particles comprise iron oxide particles; wherein the thickness is from 10 nm to less than 500 nm; and wherein the at least one pharmaceutically active ingredient comprises a photolabile pharmaceutically active ingredient.

* * * * *